United States Patent
Eslami et al.

(10) Patent No.: US 11,445,159 B2
(45) Date of Patent: Sep. 13, 2022

(54) CONTEXT-SENSITIVE WHITE BALANCING FOR SURGICAL MICROSCOPES

(71) Applicant: Carl Zeiss Meditec AG, Jena (DE)

(72) Inventors: Abouzar Eslami, Munich (DE); Corinna Maier-Matic, Munich (DE); Thorsten Tritschler, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 110 days.

(21) Appl. No.: 17/109,813

(22) Filed: Dec. 2, 2020

(65) Prior Publication Data

US 2021/0176443 A1    Jun. 10, 2021

(30) Foreign Application Priority Data

Dec. 5, 2019 (DE) .......................... 102019133174.9

(51) Int. Cl.
*G06T 7/00* (2017.01)
*H04N 9/73* (2006.01)
(Continued)

(52) U.S. Cl.
CPC ............ *H04N 9/735* (2013.01); *G06K 9/6256* (2013.01); *G06T 7/90* (2017.01); *G06V 10/95* (2022.01); *H04N 13/15* (2018.05); *H04N 13/189* (2018.05); *H04N 13/239* (2018.05); *H04N 13/257* (2018.05); *G06T 2207/10012* (2013.01);
(Continued)

(58) Field of Classification Search
CPC ...... H04N 9/735; H04N 13/15; H04N 13/189; H04N 13/239; H04N 13/257; H04N 13/133; H04N 13/296; G06K 9/6256; G06T 7/90; G06T 2207/10012; G06T 2207/10056; G06T 2207/20084; G06T 2207/10024; G06T 2207/20081; G06T 2207/30041; G06T 5/009; G06T 5/50; G06V 10/95; G06V 2201/033; G06V 2201/034; G06V 2201/10; G06V 10/454; G06V 10/82;
(Continued)

(56) References Cited

U.S. PATENT DOCUMENTS

2015/0065803 A1* 3/2015 Douglas ............. A61B 1/00045
600/200
2016/0104284 A1* 4/2016 Maguire .................. G06T 7/80
348/187

(Continued)

OTHER PUBLICATIONS

Office Action, German Application No. DE 10 2019 133 174.9, dated Aug. 19, 2020, 8 pages.

*Primary Examiner* — Howard D Brown, Jr.
(74) *Attorney, Agent, or Firm* — Honigman LLP; Brett A. Krueger

(57) ABSTRACT

A computer-implemented method and a corresponding system for context-sensitive white balancing for a stereomicroscope are presented. The method comprises recording a first digital image by way of a first camera in a first optical path of the stereomicroscope, and recording a second digital image by way of a second camera in a second optical path of the stereomicroscope. Furthermore, the method comprises determining, by means of a trained machine learning system, the context identified in the images, and determining, by means of the trained machine learning system, camera parameters suitable for controlling color channels of the first and second cameras for white balancing.

17 Claims, 5 Drawing Sheets

(51) Int. Cl.
  *G06K 9/62* (2022.01)
  *H04N 13/257* (2018.01)
  *G06T 7/90* (2017.01)
  *H04N 13/239* (2018.01)
  *H04N 13/15* (2018.01)
  *H04N 13/189* (2018.01)
  *G06V 10/94* (2022.01)

(52) U.S. Cl.
  CPC ............... *G06T 2207/10056* (2013.01); *G06T 2207/20084* (2013.01); *G06V 2201/033* (2022.01); *G06V 2201/034* (2022.01); *G06V 2201/10* (2022.01)

(58) Field of Classification Search
  CPC .... G06V 20/693; A61B 3/0025; A61B 3/132; G02B 21/0012; G02B 21/22; G02B 21/365
  See application file for complete search history.

(56) References Cited

U.S. PATENT DOCUMENTS

2017/0354013 A1* 12/2017 DeMayo ............... H05B 47/125
2020/0154538 A1* 5/2020 Smith ................... H05B 45/22

* cited by examiner

CONTEXT-SENSITIVE WHITE BALANCING FOR SURGICAL MICROSCOPES

FIELD OF THE INVENTION

The invention relates to simpler handling of surgical microscopes and, in particular, to context-sensitive, automatic direct white balancing for surgical microscopes, a corresponding system, a microscope system and a corresponding computer program product.

TECHNICAL BACKGROUND

Surgical stereomicroscopes are typically used in the medical field, in particular in ophthalmology. They are generally equipped with digital cameras in the two optical paths, the recordings of which—after corresponding processing—are used for display on one or more screens. In order that the surgeon or the treating physician is provided with as realistic an imaging as possible of the image segment captured by the surgical microscope, white balancing for the recording cameras with respect to a reference scene is indispensable. For this purpose, typically, a white pattern—e.g. a piece of white paper—is held in front of the respective objectives in order to enable white balancing in the recording channels according to the prevailing illumination.

This means that before every operation additional actions are required in order to carry out proper white balancing of the optical channels including the respective cameras. Such measures before an operation may additionally impose on the treating physician duties which would be better carried out automatically.

On the basis of the disadvantages of the known methods using a color pattern, an underlying object for the concept presented here is to overcome the aforementioned disadvantages of the known methods, and in particular also to present a method which can carry out white balancing within the optical channels fully automatically.

OVERVIEW OF THE INVENTION

This object is achieved by means of the method proposed here, the corresponding system, the microscope system and the associated computer program product as claimed in the independent claims. Further configurations are described by the respectively dependent claims.

According to a first aspect of the present invention, a computer-implemented method for context-sensitive white balancing for a stereomicroscope is presented. The method can comprise recording a first digital image by way of a first—in particular digital—camera in a first optical path of the stereomicroscope, and recording a second digital image by way of a second—in particular digital—camera in a second optical path of the stereomicroscope.

The method can furthermore comprise determining, by means of a trained machine learning system, the context identified in the images, and determining, by means of the trained machine learning system, camera parameters suitable for controlling color channels of the first and second cameras for—in particular automatic—white balancing.

According to a second aspect of the present invention, a system for context-sensitive white balancing for a stereomicroscope is presented. The white balancing system can comprise a first camera in a first optical path of the stereomicroscope for recording a first digital image, and a second camera in a second optical path of the stereomicroscope for recording a second digital image. Furthermore, the white balancing system can comprise a context determining unit adapted for determining, by means of a trained machine learning system, the context identified in the images, and a parameter determining unit for determining, by means of the trained machine learning system, camera parameters suitable for controlling color channels of the first and second cameras for white balancing.

In accordance with a third aspect, a microscope system is presented in which the aforementioned white balancing system is integrated.

Furthermore, embodiments can relate to a computer program product which can be accessed by a computer-usable or computer-readable medium and comprises program code for use by, from or in conjunction with a computer or other instruction processing systems. In the context of this description, a computer-usable or computer-readable medium can be any device suitable for storing, for communicating, for forwarding or for transporting the program code.

The computer-implemented method for context-sensitive white balancing for a stereomicroscope has a number of advantages and technical effects, which can also correspondingly apply to the associated system:

By virtue of the method presented, required white balancing for a surgical stereomicroscope can be obviated for a surgeon. Renewed white balancing before the next operation can likewise be obviated. This significantly reduces potential sources of error in preparation for an operation—in particular an eye operation. As a result, the operation quality and reliability, for example in eye operations, can be significantly increased. Moreover, the automatic white balancing enables time to be saved, thus resulting in a shorter treatment time for the patient.

The method presented not only ensures that the context—i.e. the imaged element during white balancing—is identified correctly, but also ensures that the context is the same in both optical paths. Moreover, the method presented can ensure that the color representations—as a result of white balancing performed beforehand—are identical. In this case, the white balancing is performed by means of an automatic determination of camera parameters for the respective optical path.

A further advantage of the method performed is that the context identification is carried out in different, parallel processing pipelines and a combination of pipeline interim results takes place only relatively at the end of the respective pipeline, from which results both the respective camera parameter values and a color consistency value can then be determined in parallel.

Further embodiments of the inventive concept for the method are presented below, which embodiments can equally and correspondingly apply to the corresponding system:

In accordance with one advantageous embodiment of the method, the camera parameters can additionally comprise a color consistency value indicative of a color difference between the first digital image and the second digital image. This makes it possible to ensure that there are no deviations between the first optical path and the second optical path, and that in particular the representation on one monitor (or separately on two monitors) also has no deviation of the representations of the first digital image and the second digital image which might possibly lead to an erroneous interpretation during an operation.

In accordance with a further advantageous embodiment of the method, the machine learning system can be represented by a network comprising a first pipeline and a second pipeline. In this case, the first pipeline can perform a processing of the first digital image and the second pipeline can perform a processing of the second digital image. In this case, the first pipeline—in particular the elements of the pipeline—can be trained to determine the identified context of the first digital image, i.e. to classify or to identify said context: e.g. on the basis of comparisons with known contexts.

The second pipeline can additionally be trained to determine or to classify or correspondingly to identify the identified context of the second digital image independently of the identified context of the first image.

In other words, the digital images captured by the digital cameras are initially processed independently of one another. Advantageously, it is possible to carry out the processing in each pipeline—although independently of one another—in the same way in parallel with one another.

In accordance with a more detailed advantageous embodiment of the method, each of the first and second pipelines can consist of a sequence of a plurality of groups. In this case, each of the groups can comprise a plurality of successive convolutional layers, followed in each case by a pooling layer. In this case, the first and second pipelines are advantageously constructed symmetrically and independently of one another, such that digital input images can be processed in parallel.

The plurality of successive convolutional layers by virtue of a concluding pooling layer need not always be identical, but rather can vary from group to group. Different substeps can thus be performed in each group. Functions such as maxpool and average can be used as pooling layers.

In accordance with a supplementary advantageous embodiment of the method, a respective classifier layer can be used at the end of the first pipeline and at the end of the second pipeline. Said classifier layer can serve to ascertain (i.e. to determine or, in the jargon of machine learning classifier systems, "predict") the context of the respective recorded digital image. The input data for said classifier layer are the output data of the preceding pooling layer of the preceding group. At the output of the classifier layers of the first and second pipelines, the contexts of the first pipeline and the second pipeline can then optionally be compared with one another. In the event of deviations with respect to one another, a corresponding alarm signal can be generated in order to make an operator aware of a malfunction.

In accordance with one advantageous embodiment of the method, skip connections can be selectively present between individual convolutional layers from among the successive convolutional layers. It is thus possible to skip one or more layers of the network within a group. The network can thus acquire the form of a so-called ResNet or ResNeXt. In this case, the network that arises can then be usable for deep residual learning. In this case, it is possible to compensate for the potentially negative effect that can arise if a very large number of levels are present in a convolutional network, the (prediction) accuracy attains a saturation region and possibly even decreases again as the number of layers increases. In this case, an interim result x before e.g. two (or more) of a further layer is combined again with the output data (vector) of the second layer and forms as it were a short cut for the data flow.

In accordance with a particular advantageous embodiment of the method, a respective interim result in the first and second pipelines after a predetermined number of layers—in particular after an identical number of layers in the two pipelines—of the network can be fed to a combination layer. In this case, the two interim result vectors can be concatenated (concatenation). The vector length would thus double.

In accordance with a development advantageous embodiment of the method, the combination layer can be a beginning of a third pipeline in the machine learning system. In this case, the third pipeline can comprise a further group of a plurality of successive convolutional layers and/or pooling layers after the combination layer. In one case, only one group is present, i.e. one or more layers of convolutional layers and a pooling layer. An interim result at the end of the third pipeline can then be fed to a—for example fully connected—regression network as input data, wherein the regression network comprises the determined camera parameters as output data. Thus the white balancing can then be produced. Besides the convolutional layers mentioned, the regression network or the associated regression layer can also be a deep neural network as well.

In accordance with an additionally development advantageous embodiment of the method, the interim result at the end of the third pipeline can be also fed to a—e.g. for example fully connected—classifier system as input data, wherein the classifier system comprises the abovementioned color consistency value as output data.

The classifier system can thus e.g. operate in parallel and thus independently with respect to the regression network and generate an indicator of whether the processing in both pipelines has proceeded homogeneously, i.e. the same parameters are present for the control of the cameras or—if the cameras have deviating properties—the color channels are influenced in such a way that the same result (within a tolerance threshold that is no longer perceptible) would be displayed on the screen for the observer as a result.

In accordance with a beneficial embodiment, the camera parameters for at least one color channel can comprise a correction value in order to control the white balancing. One correction value per color channel can typically be generated in this case. Moreover, the proposed concept is independent of the color space or color model respectively used (e.g. RGB, CMY, RGBCMY, etc.).

In accordance with a supplementary advantageous embodiment of the method, the machine learning system can be a deep neural network (deep, multilayered neural network), a decision tree system or a random forest system. The basic function can be realized with all types of network.

In accordance with one possible advantageous embodiment, the method can furthermore comprise training the machine learning system with a set of pairs of digital images—in particular training images —, wherein each pair corresponds to a respective imaging from the first optical path and the second optical path. The training takes place by means of a process for machine learning in order to effect generation of a (learning) model for determining the context from each image and for determining the camera parameters and/or a color consistency value. In this case, the color consistency value can be indicative of a color deviation between the recorded images of the first and second cameras. In addition to the training data—or as part thereof—further test data can be available in order to be able to assess the reliability or quality of the behavior of the machine learning system (referred to as prediction quality). The training can ideally be carried out with digital images which were recorded under conditions of white light and enable an ideal imaging of the tissue. Moreover, the training data set should comprise a plurality of images having color casts and should comprise corresponding annotations in order to train the system with a multiplicity of color casts and the compensation thereof.

The learning system can be a system or a method for supervised learning and the images of the set of digital images for supervised learning can be annotated with metadata for generating the learning model. This procedure allows an efficient learning or training process.

In accordance with a supplementary embodiment of the method, the images of the set of pairs of digital images can be generated at least partly by means of an image generator. This makes it possible to significantly reduce the outlay produced by real recorded images.

In accordance with one embodiment of the method, the identified context can be a predefined type of tissue, a bone—in particular a skull bone, an instrument, or a sensor, for example. The tissue can be, in particular, a retina or sclera of an eye. Furthermore, in another application, the tissue can be surface skin of a body, such that the method presented here is usable not only in eye operations but also in operations concerning skin cancer.

OVERVIEW OF THE FIGURES

It should be pointed out that exemplary embodiments of the invention may be described with regard to different implementation categories. In particular, some exemplary embodiments are described with regard to a method, while other exemplary embodiments may be described in the context of corresponding devices. Irrespective of this, it is possible for a person skilled in the art, from the description hereinabove and hereinbelow here—unless indicated otherwise—to recognize and to combine possible combinations of the features of the method and also possible feature combinations with the corresponding system, even if they belong to different claim categories.

Aspects already described above and additional aspects of the present invention are evident, inter alia, from the exemplary embodiments described and from the additional further specific configurations described by reference to the figures.

Preferred exemplary embodiments of the present invention will be described by way of example and with reference to the following figures.

DETAILED DESCRIPTION OF THE FIGURES

Figure 1:
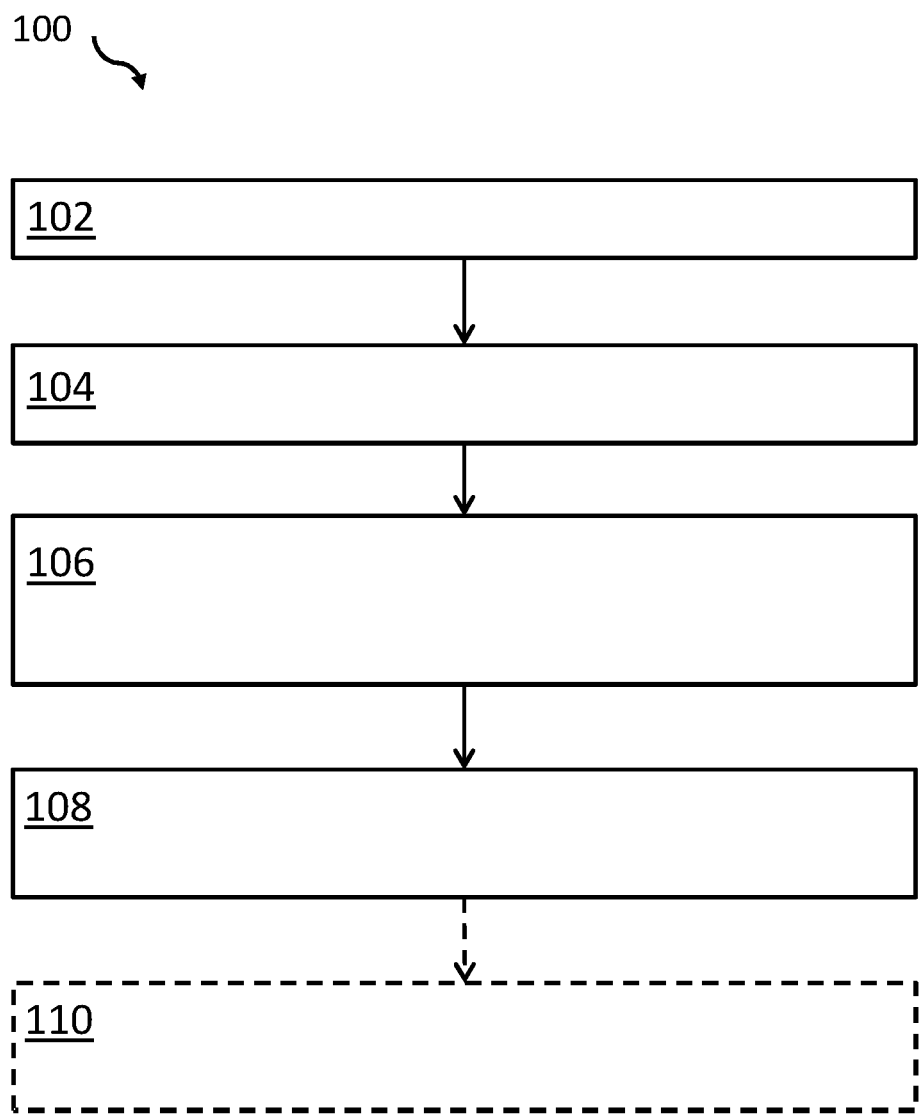
FIG. 1 illustrates a block diagram of one exemplary embodiment of the inventive computer-implemented method for context-sensitive white balancing for a stereomicroscope.

In the context of this description, conventions, terms and/or expressions are intended to be understood as follows:

In the context of the present document, the term "context-sensitive white balancing" describes the process of color correction for image sensors of a stereomicroscope, such that images of the image sensors that are represented on monitors enable an optimum imaging of the represented object of the stereomicroscope for an observer. In other words, the camera(s)—or the associated image sensors and the associated image processing—is/are sensitized to the color temperature of the light at the recording location. Practically the ability of the human eye with regard to chromatic adaptation is thus simulated. Moreover, the represented context—for example the retina of an eye—of the images recorded by the image sensors is identified, classified and taken into account in the white balancing.

The term "stereomicroscope" describes a light microscope in which a separate beam path is provided for both eyes. Prospective vision ("stereo effect") is achieved by virtue of the different viewing angles in the two associated beam paths. In the case of the surgical microscopes used here, this effect is achieved by means of separate cameras for each of the two beam paths and a corresponding independent image processing. The two separate beam paths are also referred to here as first optical path and second optical path.

The term "camera parameter"—in particular camera parameter value—here describes at least one signal which can influence the color temperature of the image sensor or the associated image processing in order to represent the associated image represented on a monitor with an optimum color temperature.

The term "color consistency value" describes a value indicating a measure of the equality of the color temperatures of the two digital images in the two optical paths with regard to the image processing pipelines. Ideally the two images represented on the monitors are of the same color temperature.

The term "color model or color space" essentially denotes the color channel composition and the interaction thereof for the individually recorded and processed color signals in individual channels of the signal processing. In principle, the method proposed here can be used for any known color model. Examples are: RGB (red green blue) or CMY(K) (cyan, magenta, yellow, (black)). The signals for the individual color channels firstly—proceeding from the camera or the camera sensor—are processed (for example amplified, normalized) separately from one another and can then be processed jointly by the method presented here or the parallel system.

The term "pipeline" describes a sequence of elements used to process input data (substantially from a digital camera) in order to generate results such as a color consistency value, an identified context and/or camera parameters. In this case, the elements are substantially layers having different tasks with regard to the processing of the signals.

The pipeline can consist of a plurality of groups of elements. In this case, a plurality of convolutional layers are typically followed by a pooling layer. The output data of a layer are used in each case as input data for the next layer. In this case, a pooling layer is essentially used to reduce the number of spatial dimensions in a targeted manner, whereby the required computing power can be reduced. Maxpool and average can be mentioned as examples of pooling layers.

Each of the pipelines used here can be regarded as a dedicated CNN (convolutional neural network).

The term "skip connection" describes a bridging of one or more convolutional layers of the CNN. In this case, output data of a convolutional layer are combined again with output data of a downstream convolutional layer and used as input data for a next convolutional layer. This enables an improvement of identified (classified) contexts by the CNN.

The term "regression network" here describes a neural network which can be used to determine (predict) dependencies between dependent variables and one or more independent variables. Models both of linear regression and of polynomial regression or logarithmic regression can be used here.

The term "digital image" here describes an imaging or the result of generation of an amount of data in the form of pixel data of an object that really exists: here a retina of an eye, for example. In a generalized way, a "digital image" can be understood as a two-dimensional signal matrix. The individual vectors of the matrix can also be concatenated in order thus to generate an input vector for a layer of a CNN. The digital images can also be individual frames of video sequences.

The term "classify" describes the process of assigning a recorded image or parts thereof—here in particular individual pixels of the recorded image—to pixel classes. One pixel class can describe for example the fact that the corresponding pixel belongs to an image segment which is defect-free, while another pixel class can describe the fact that a defect on/in the test specimen is involved. Moreover, it is possible to specify a probability value for this statement. The instrument for carrying out the classifying is the classifier system in the context of this text.

The term "machine learning" is a basic term or a basic function of artificial intelligence, wherein e.g. statistical methods are used to give computer systems the ability of "learning". By way of example, this involves optimizing specific patterns of behaviour within a specific range of tasks. The methods used enable trained machine learning systems to analyse data, without this necessitating explicit procedural programming. Typically, for example, an NN (neural network) or CNN (convolutional neural network) is an example of a system for machine learning to form a network of nodes which act as artificial neurons and to form artificial connections between the artificial neurons—so-called links—wherein the artificial connections can be assigned parameters—for example weight parameters for the connection. During the training of the neural network, the weight parameter values of the connections are automatically adapted on the basis of input signals for generating a desired result. In supervised learning, the images supplied as input values (training data)—generally (input) data—are supplemented by desired output data (annotations) in order to generate a desired output value (desired class). When considered in a very general way, a mapping of input data to output data is learned.

The term "classifier system"—also referred to as classifier or classification system in the context of machine learning—describes a machine learning-based system which, by means of training with training data, is enabled to assign input data—here in particular image data of recorded digital images—features of the images to a specific class (e.g. defective/not defective) in order thus to identify (or predict) a context.

It should also be noted here that a classification system typically classifies into a predefined number of classes. This is normally done by a classification value of the input data being determined for each class and a WTA filter (winner takes it all) selecting the class having the highest classification value as the classified class. In classifiers, the deviation with respect to a 100% classification value is often used as a quality parameter of the classification or as a probability for the correctness of the classification.

Examples of classifier systems which are usable for the subjects of the inventive concepts presented here are systems based on the following principles: support vector machine, random forest, decision tree, nearest neighbor, logistical regression and neural network. Further algorithms are also possible, of course.

The term "training the classification system" means here that e.g. a machine learning system is adjusted by means of a plurality of sets of exemplary data—i.e. reference data—in a neural network, for example, by means of partly repeated evaluation of the exemplary data so as to assign, after the training phase, even unknown image data to one or more classes with which the learning system has been trained. The exemplary data are typically annotated—i.e. provided with metadata—in order to generate desired results on the basis of the input images.

The term "convolutional neural network" (CNN)—as an example of a classifier/classifier system—describes a class of artificial neural networks based on feedforward techniques. They are often used for image analyses with images or the pixels thereof as input data. The main constituent of convolutional neural networks here is convolutional layers (hence the name), enabling an efficient evaluation by means of parameter sharing. Typically, each pixel of the recorded image is allocated to an artificial neuron of the neural network as input value.

It should also be mentioned that deep neural networks consist of a plurality of layers having different functions—for example an input layer, an output layer and one or more intervening layers, for example for convolution operations, application of non-linear functions, reduction of dimensions, normalization functions, etc. The functions can be "implemented in software", or specific hardware assemblies can perform the calculation of the respective function values. The nodes can then consist of a memory for weight parameters and one or more signal amplifiers. Combinations of hardware and software elements are furthermore usable.

A detailed description of the figures is specified below. It goes without saying here that all details and statements in the figures are illustrated schematically. Firstly, a block diagram of one exemplary embodiment of the computer-implemented method according to the invention for context-sensitive white balancing is illustrated. Further exemplary embodiments and exemplary embodiments of the corresponding system are described subsequently:

FIG. 1 illustrates a block diagram of one exemplary embodiment of the inventive computer-implemented method 100 for context-sensitive white balancing for a stereomicroscope—e.g. a surgical microscope. In this case, the method 100 comprises recording, 102, a first digital image by way of a first—in particular digital—camera in a first optical path of the stereomicroscope, and recording, 104, a second digital image by way of a second (also digital) camera in a second optical path of the stereomicroscope.

The method 100 furthermore comprises determining, 106, (i.e. predicting), by means of a trained machine learning system, the context (for example the retina) identified in the images—in particular in the first and second images —, and determining, 108, by means of the trained machine learning system, camera parameters. In this case, the camera parameters are suitable for controlling color channels of the first and second cameras such that automatic white balancing is achieved. Moreover, the optional process of determining 110 a color consistency value is illustrated.

Figure 2:
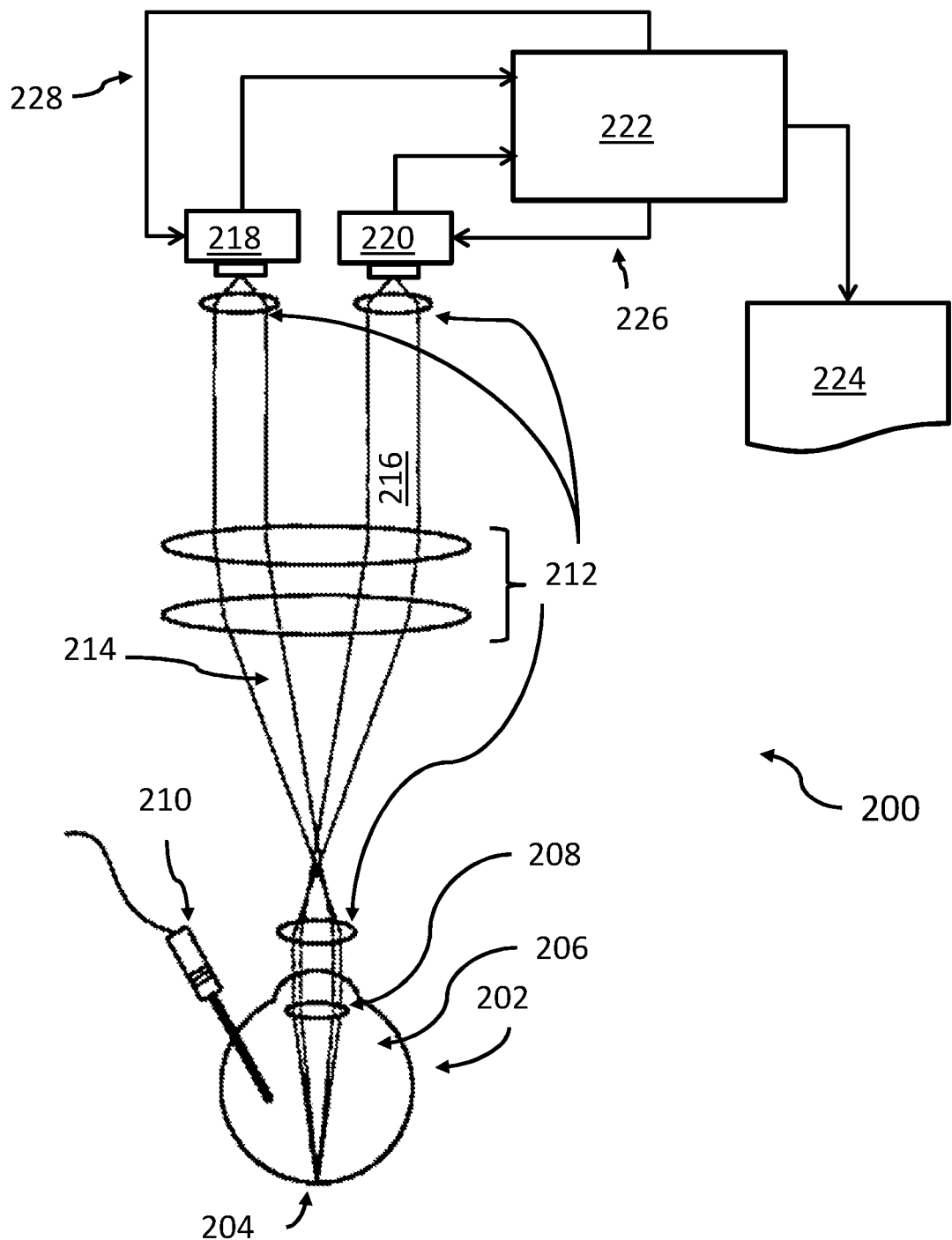
FIG. 2 illustrates a typical schematic set-up of a stereomicroscope with associated recording and evaluation functions.

FIG. 2 illustrates a typical schematic set-up of a stereomicroscope with associated recording and evaluation functions. In this case, in order to illuminate the retina 204 of the eye 202, an illumination 210 is introduced into the eyeball 206. The beam paths—or the optical paths 214 and 216—extend from the retina 204 through the natural lens 208 of the eye (optionally an artificially inserted lens) and a lens system 212, which in the example illustrated is formed from two large lenses in the center, a lower objective lens directly at the eye and respective lenses in front of the cameras 218, 220.

The signals of the digital cameras 218 and 220 are processed by an evaluation unit 222 (e.g. video processing unit) and represented on one or more screens 224. Besides typical image processing units, the evaluation unit 222 can also comprise the proposed white balancing system. The required parameter values for white balancing for the digital cameras 218 and 222 are illustrated as feedback channels 226 and 228. It goes without saying here that the feedback channels 226 and 228 can each transport a plurality of camera parameter values either in parallel or in series.

Figure 3:
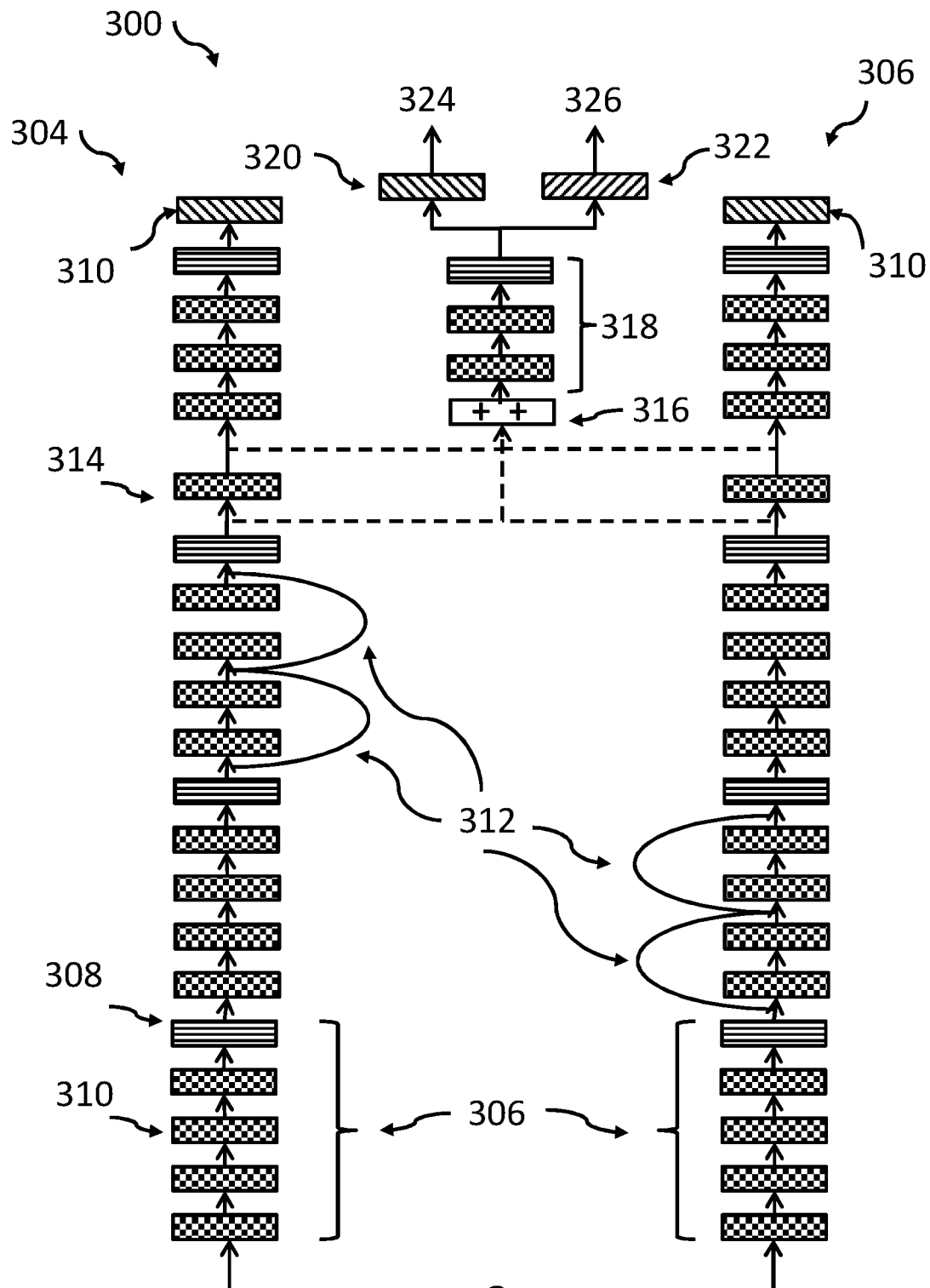
FIG. 3 illustrates a block diagram of one exemplary embodiment of the pipelines.

FIG. 3 illustrates a block diagram of one exemplary embodiment of the method and of a white balancing system 300 for context-sensitive white balancing. It can be integrated in the evaluation unit 222 (cf. FIG. 2). The first and second pipelines are represented by the reference signs 304 and 306. They consist of different layers, represented as individual blocks lying one above another in a deep neural network. The layers are identified in a plurality of successive groups—one of the latter is identified by the reference sign 306. Each of these groups comprises at least one, typically a plurality of convolutional layers 310 and a concluding pooling layer 308. So-called skipper or bridging connections 312 (some of which are illustrated by way of example) can be present within the individual groups. The groups can be set up in principle; i.e. they typically have a different number of different types of convolutional layers 310. At the lower end of each of the two pipelines 304, 306, the digital signals of the digital cameras (cf. FIG. 2, 218, 220) can be fed to the pipelines directly or after having been preprocessed.

Upstream and respectively downstream of the convolutional layer 314 in the first pipeline 304 (and correspondingly in the second pipeline), signal paths, coupled out from the respective pipeline 304, 306, lead to a combination layer 316, in which the two interim results coupled out from the first pipeline 304 and the second pipeline 306 are combined for example by concatenation. The vector length of the interim result would typically double as a result. However, other possibilities for combination of the two interim results are also conceivable.

The combination layer 316 is followed by one (or more) new group(s) 318 of one or more convolutional layers and a concluding pooling layer (represented by horizontal stripes).

The output vector from the last pooling layer is fed both to a classifier layer 320 (or a classifier system) and to a regression layer 322 (or a regression network). The output 324 of the classifier layer 320 represents the color consistency value between the two cameras, while the output 326 of the regression layer 322 represents the parameter values for the digital cameras for white balancing.

It should additionally be pointed out that a respective classifier layer 310 is present at the end (last illustrated layer of the first and second pipelines). These classifier layers yield as output values a class of the captured and identify context on which the respective associated camera focusses.

Figure 4:
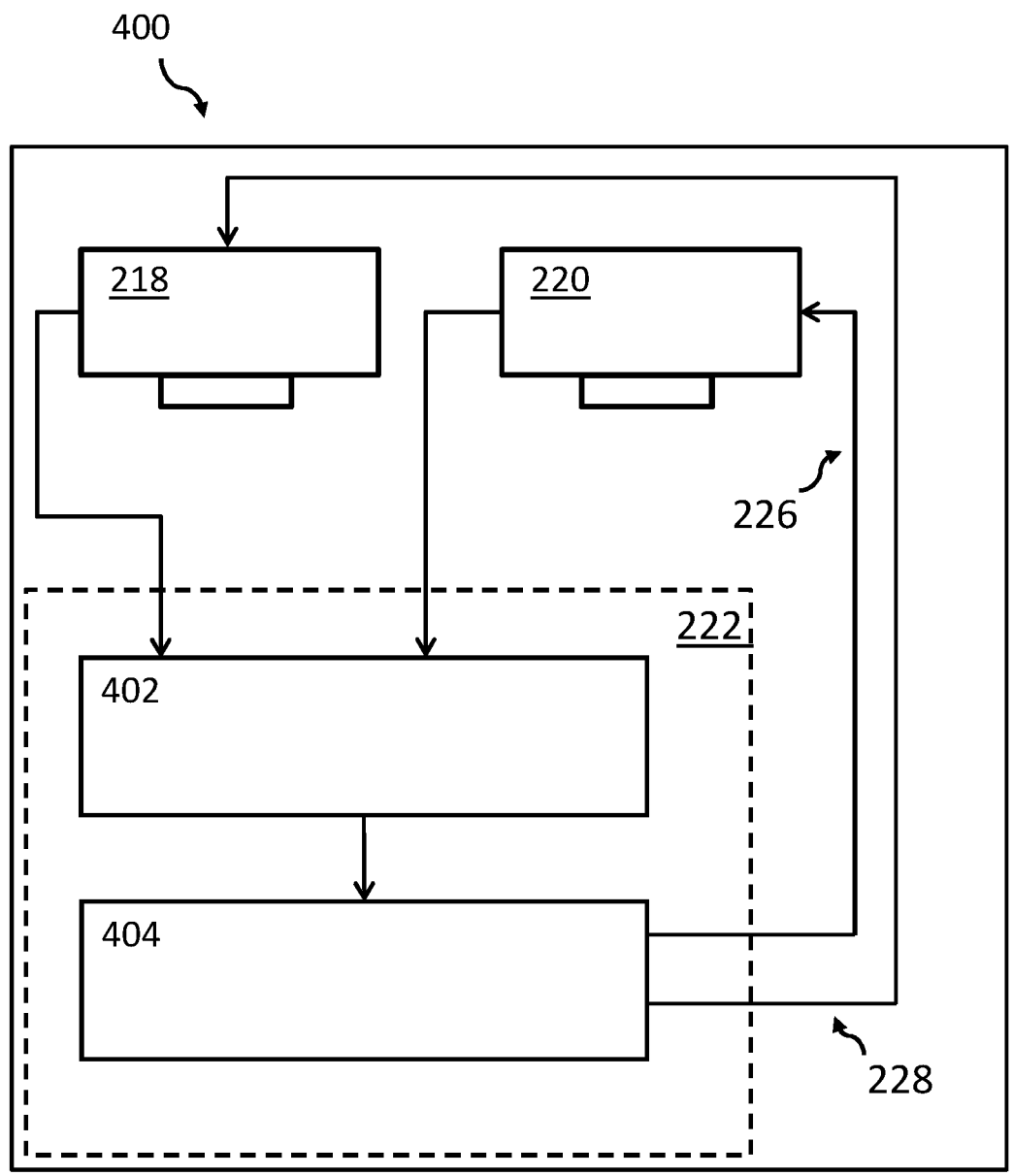
FIG. 4 illustrates a block diagram of a white balancing system for context-sensitive white balancing for a stereomicroscope.

For the sake of completeness, FIG. 4 symbolically illustrates a block diagram of a white balancing system 400 for context-sensitive white balancing for a stereomicroscope. The white balancing system comprises a first camera 218 (cf. FIG. 2) in a first optical path 214 (cf. FIG. 2) of the stereomicroscope, for recording a first digital image and a second camera 220 (cf. FIG. 2) in a second optical path 216 (cf. FIG. 2) of the stereomicroscope for recording a second digital image.

Furthermore, the white balancing system 400 comprises a context determining unit 402 adapted for determining, by means of a trained machine learning system, the context identified in the images, and a parameter determining unit 404 for determining, by means of the trained machine learning system, camera parameters suitable for controlling color channels of the first and second cameras for white balancing. This feedback produced in this way is represented symbolically by the connections 226, 228 from the processing unit 222 (also cf. FIG. 2) to the cameras, said processing unit comprising, inter alia, the two units of context determining unit 402 and parameter determining unit 404. The return channels 226 and 228 (cf. FIG. 2) are additionally illustrated, which can act on the cameras 218 and 220 for the white balancing.

Figure 5:
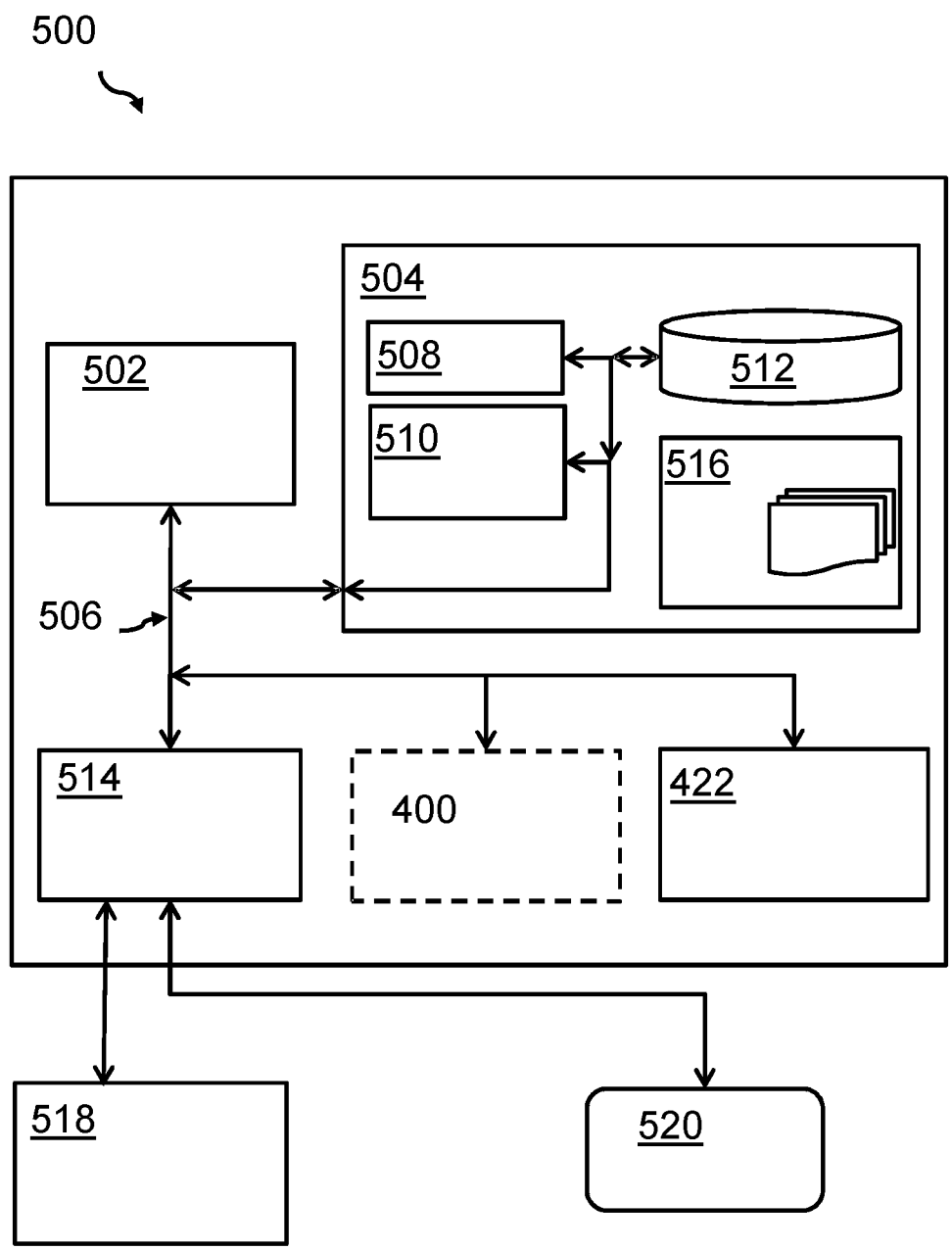
FIG. 5 illustrates a block diagram of a computer system which additionally can wholly or partly comprise the system in accordance with FIG. 4.

FIG. 5 illustrates a block diagram of a computer system which can comprise at least parts of the white balancing system for context-sensitive white balancing for the stereomicroscope. Embodiments of the concept proposed here can be used, in principle, with practically any type of computer, independently of the platform used therein for storing and/or executing program codes. FIG. 5 illustrates by way of example a computer system 500 suitable for executing program code according to the method presented here. A computer system already present in a microscope system can also serve—if appropriate with corresponding extensions—as a computer system for implementing the concept presented here.

The computer system 500 comprises a plurality of general purpose functions. In this case, the computer system can be a tablet computer, a laptop/notebook computer, some other portable or mobile electronic device, a microprocessor system, a microprocessor-based system, a smartphone or a computer system having specially designed special functions, or else part of a microscope system. The computer system 500 can be designed for executing instructions executable by the computer system—such as, for example, program modules—which can be executed in order to implement functions of the concepts proposed here. For this purpose, the program modules can have routines, programs, objects, components, logic, data structures, etc., in order to implement specific tasks or specific abstract data types.

The components of the computer system can comprise the following: one or a plurality of processors or processing units 502, a memory system 504 and a bus system 506, which connects various system components including the memory system 504 to the processor 502. The computer system 500 typically comprises a plurality of volatile or non-volatile memory media that can be accessed by the computer system 500. In the memory system 504 it is possible to store the data and/or instructions (commands) of the memory media in volatile form—such as, for example, in a RAM (random access memory) 508—in order to be executed by the processor 502. These data and instructions realize individual or a plurality of functions and/or steps of the concept presented here. Further components of the memory system 504 may be a permanent memory (ROM) 510 and a long-term memory 512, in which the program modules and data (reference sign 516) and also workflows can be stored.

The computer system comprises a number of dedicated devices for communication (keyboard 518, mouse/pointing device (not illustrated), screen 520, etc.). These dedicated devices can also be combined in a touch-sensitive display.

An I/O controller 514 provided separately ensures smooth data exchange with external devices. A network adapter 522 is available for communication via a local or global network (LAN, WAN, for example via the Internet). The network adapter can be accessed by other components of the computer system 500 via the bus system 506. It goes without saying here that—although not illustrated—other devices can also be connected to the computer system 500.

Furthermore, at least parts of the system 400 for context-sensitive white balancing for the stereomicroscope (cf. FIG. 4) can be connected to the bus system 506.

The description of the various exemplary embodiments of the present invention was presented in order to afford a better understanding, but does not serve to directly restrict the inventive concept to these exemplary embodiments. Further modifications and variations are inferred by the person skilled in the art himself/herself. The terminology used here was chosen so as to best describe the fundamental principles of the exemplary embodiments and to make them easily accessible to the person skilled in the art.

The principle presented here can be embodied as a system, as a method, as combinations thereof and/or else as a computer program product. In this case, the computer program product can comprise one (or a plurality of) computer-readable storage medium/media having computer-readable program instructions in order to cause a processor or a control system to implement various aspects of the present invention.

As media, use is made of electronic, magnetic, optical, electromagnetic, infrared media or semiconductor systems as forwarding medium; for example SSDs (solid state device/drive as solid state memory), RAM (random access memory) and/or ROM (read-only memory), EEPROM (electrically erasable ROM) or any desired combination thereof. Suitable forwarding media also include propagating electromagnetic waves, electromagnetic waves in waveguides or other transmission media (e.g. light pulses in optical cables) or electrical signals transmitted in wires.

The computer-readable storage medium can be an embodying device that keeps available or stores instructions for use by an instruction executing device. The computer-readable program instructions described here can also be downloaded to a corresponding computer system, for example as a (smartphone) app from a service provider via a cable-based connection or a mobile radio network.

The computer-readable program instructions for performing operations of the invention described here can be machine-dependent or machine-independent instructions, microcode, firmware, status-defining data or any source code or object code written for example in C++, Java or similar programming languages or in conventional procedural programming languages such as, for example, the programming language "C" or similar programming languages. The computer-readable program instructions can be executed completely by a computer system. In some exemplary embodiments, there may also be electronic circuits, such as, for example, programmable logic circuits, field-programmable gate arrays (FPGA) or programmable logic arrays (PLA), which execute the computer-readable program instructions by using status information of the computer-readable program instructions in order to configure or to individualize the electronic circuits according to aspects of the present invention.

Furthermore, the invention presented here is illustrated with reference to flow diagrams and/or block diagrams of methods, devices (systems) and computer program products according to exemplary embodiments of the invention. It should be pointed out that practically any block of the flow diagrams and/or block diagrams can be configured as computer-readable program instructions.

The computer-readable program instructions can be made available to a general purpose computer, a special computer or a data processing system programmable in some other way, in order to produce a machine, such that the instructions that are executed by the processor or the computer or other programmable data processing devices generate means for implementing the functions or processes illustrated in the flow diagram and/or block diagrams. These computer-readable program instructions can correspondingly also be stored on a computer-readable storage medium.

In this sense any block in the illustrated flow diagram or block diagrams can represent a module, a segment or portions of instructions representing a plurality of executable instructions for implementing the specific logic function. In some exemplary embodiments, the functions represented in the individual blocks can be implemented in a different order—optionally also in parallel.

The illustrated structures, materials, sequences and equivalents of all means and/or steps with associated functions in the claims hereinafter are intended to apply all structures, materials or sequences as expressed by the claims.

REFERENCE SIGNS

100 Method for context-sensitive white balancing
102 Method step appertaining to 100
104 Method step appertaining to 100
106 Method step appertaining to 100
108 Method step appertaining to 100
110 Optional method step appertaining to 100
200 Procedure of the underlying concept presented here
202 Eye
204 Retina
206 Interior of eye
208 Lens of eye
210 Illumination
212 Lens system
214 Optical path
216 Optical path
218 Camera
220 Camera
222 Evaluation unit
224 Screens
226 Feedback channel
228 Feedback channel
300 Layers of the neural network
304 First pipeline
306 Second pipeline
306 Group
308 Pooling layer
310 Classifier layer
312 Skip connection
314 Convolutional layer
316 Combination layer
318 Group of the third pipeline
320 Classifier layer
322 Regression layer
324 Output for color consistency value
326 Output for parameter values for a camera
400 White balancing system
402 Context determining unit
404 Parameter determining unit
502 Processor 504 Memory system
506 Bus system
508 RAM
510 ROM
512 Long-term memory
514 I/O controller
516 Program modules, potential data
518 Keyboard
520 Screen
522 Network adapter

The invention claimed is:

1. A computer-implemented method for context-sensitive white balancing for a stereomicroscope, the method comprising:
recording a first digital image by way of a first camera in a first optical path of the stereomicroscope;
recording a second digital image by way of a second camera in a second optical path of the stereomicroscope;
determining, by means of a trained machine learning system, the context identified in the images; and
determining, by means of the trained machine learning system, camera parameters suitable for controlling color channels of the first and second cameras for white balancing,
wherein the machine learning system is represented by a network comprising a first pipeline and a second pipeline,
wherein the first pipeline performs a processing of the first digital image,
wherein the second pipeline performs a processing of the second digital image,
wherein the first pipeline is trained to determine the identified context of the first digital image and
wherein the second pipeline is trained to determine the identified context of the second digital image independently of the identified context of the first image.

2. The method of claim 1, wherein the camera parameters additionally comprise a color consistency value indicative of a color difference between the first digital image and the second digital image.

3. The method of claim 1, wherein a respective classifier layer is used at the end of the first pipeline and at the end of the second pipeline.

4. The method of claim 1, wherein each of the first and second pipelines consists of a sequence of a plurality of groups, wherein each of the groups comprises a plurality of successive convolutional layers, followed in each case by a pooling layer.

5. The method of claim 4, wherein skip connections are selectively present between individual convolutional layers from among the successive convolutional layers.

6. The method of claim 4, wherein a respective interim result in the first and second pipelines after a predetermined number of layers of the network is fed to a combination layer.

7. The method of claim 6, wherein the combination layer is a beginning of a third pipeline in the machine learning system, wherein the third pipeline comprises a further group of a plurality of successive convolutional layers and/or pooling layers after the combination layer and an interim result at the end of the third pipeline is fed to a regression network as input data, wherein the regression network comprises the determined camera parameters as output data.

8. The method of claim 7, wherein the interim result at the end of the third pipeline is also fed to a classifier system as input data, wherein the classifier system comprises the color consistency value as output data.

9. The method of claim 1, wherein the camera parameters for at least one color channel comprise a correction value in order to control the white balancing.

10. The method of claim 1, wherein the machine learning system comprises a deep neural network, a decision tree system or a random forest system.

11. The method of claim 1, further comprising training the machine learning system with a set of pairs of digital images, wherein each pair corresponds to a respective imaging from the first optical path and the second optical path, by means of machine learning for generating a learning model for determining the context from each image and for determining the camera parameters and/or a color consistency value indicative of a color deviation between the recorded images of the first and second cameras.

12. The method of claim 11, wherein the images of the set of pairs of digital images are generated at least partly by means of an image generator.

13. The method of claim 1, wherein the learning system comprises a system for supervised learning, and wherein the images of the set of digital images for supervised learning are annotated with metadata for generating the learning model.

14. The method of claim 1, wherein the identified context comprises a predefined type of tissue, a bone, an instrument, or a sensor.

15. A white balancing system for context-sensitive white balancing for a stereomicroscope, the white balancing system comprising:
a first camera in a first optical path of the stereomicroscope for recording a first digital image;
a second camera in a second optical path of the stereomicroscope for recording a second digital image;
a context determining unit adapted for determining, by means of a trained machine learning system, the context identified in the images; and
a parameter determining unit for determining, by means of the trained machine learning system, camera parameters suitable for controlling color channels of the first and second cameras for white balancing,
wherein the machine learning system is represented by a network comprising a first pipeline and a second pipeline,
wherein the first pipeline performs a processing of the first digital image and wherein the second pipeline performs a processing of the second digital image,
wherein the first pipeline is trained to determine the identified context of the first digital image, and
wherein the second pipeline is trained to determine the identified context of the second digital image independently of the identified context of the first image.

16. A microscope system comprising the white balancing system of claim 15.

17. A computer program product for context-sensitive white balancing for a stereomicroscope, wherein the computer program product comprises a computer-readable storage medium comprising program instructions stored thereon, wherein the program instructions are executable by one or a plurality of computers or control units and cause the one or the plurality of computers or control units to carry out the method of claim 1.

* * * * *